US00PP35106P2

(12) United States Plant Patent
Holtmaat

(10) Patent No.: US PP35,106 P2
(45) Date of Patent: Apr. 11, 2023

(54) ***HEUCHERA* PLANT NAMED 'TONCKA 308'**

(50) Latin Name: ***Heuchera* hybrid**
Varietal Denomination: Toncka 308

(71) Applicant: Henricus Maria Joseph Holtmaat, Zuidwolde (NL)

(72) Inventor: Henricus Maria Joseph Holtmaat, Zuidwolde (NL)

(73) Assignee: AB KWEKERSRECHTEN B.V., Zuidwolde (NL)

( * ) Notice: Subject to any disclaimer, the term of this patent is extended or adjusted under 35 U.S.C. 154(b) by 0 days.

(21) Appl. No.: 17/961,677

(22) Filed: Oct. 7, 2022

(30) Foreign Application Priority Data

Nov. 11, 2021 (QZ) ..... PBR 20212921

(51) Int. Cl.
*A01H 5/12* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ... A01H 5/12; A01H 5/00; A01H 5/02; A01H 6/80
See application file for complete search history.

(56) References Cited

U.S. PATENT DOCUMENTS

PP24,525 P3 * 6/2014 Egger ..... A01H 6/80 Plt./440

* cited by examiner

*Primary Examiner* — June Hwu
(74) *Attorney, Agent, or Firm* — Penny J Aguirre

(57) ABSTRACT

A new cultivar of *Heuchera* plant named 'Toncka 308' that is characterized by its leaves that are moderately to strongly undulate, its young leaves that are grey-red in color, its mature leaves with grey-purple to brown on the upper surface and grey-purple on the lower surface, and its low number of inflorescences.

2 Drawing Sheets

Botanical classification: *Heuchera* hybrid.
Cultivar designation: 'Toncka 308'.

CROSS REFERENCE TO A RELATED APPLICATION

This application claims priority to European Community Plant Variety Office (CPVO) Plant Breeder's Rights Application No. No. 2021/2921, filed Nov. 11, 2021. The Applicant received the information for the Plant breeders' rights application directly from the Inventor.

BACKGROUND OF THE INVENTION

The present invention relates to a new and distinct cultivar of *Heuchera* of hybrid origin, botanically known as *Heuchera* 'Toncka 308' and is hereinafter referred to by its cultivar name 'Toncka 308'.

The new cultivar was discovered as a chance seedling in a trial field by the Inventor in Zuidwolde, The Netherlands in July of 2019. The source of the seedling was from seed collected in 2019 from open pollinated plants in a trial field that contained numerous unnamed and unpatented proprietary *Heuchera* seedlings from the Inventor's breeding program. The parentage of 'Toncka 308' is therefore unknown.

Asexual propagation of the new cultivar was first accomplished under the direction of the Inventor by tissue culture initiated from meristem tissue in February of 2021 in Heerhugowaard, The Netherlands. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Toncka 308' as a new and unique cultivar of *Heuchera*.

1. 'Toncka 308' exhibits leaves that are moderately to strongly undulate.
2. 'Toncka 308' exhibits young leaves that are grey-red in color.
3. 'Toncka 308' exhibits mature leaves with grey-purple to brown on the upper surface and grey-purple on the lower surface.
4. 'Toncka 308' exhibits a low number of inflorescences.

'Toncka 308' can be most closely compared to the *Heuchera* cultivars 'Fire Alarm' (U.S. Plant Pat. No. 24,525) and 'Peach Flambe' (U.S. Plant Pat. No. 17,195). 'Fire Alarm' is similar to 'Toncka 308' in plant size and leaf size. 'Fire Alarm' differs from 'Toncka 308' in having foliage that is lighter and more pink-red in color and in producing more flowers that are white in color. 'Peach Flambe' is similar to 'Toncka 308' in leaf size. 'Peach Flambe' differs from 'Toncka 308' in having foliage that is lighter and more pink-red in color and flowers that are white in color.

BRIEF DESCRIPTION OF THE DRAWINGS

The accompanying color photographs illustrate the overall appearance and distinct characteristics of the new *Heu-*

*chera*. The photographs were taken of a plant 18 months in age of the new cultivar as grown outdoors in a 19-cm container in Zuidwolde, The Netherlands.

Figure 1:
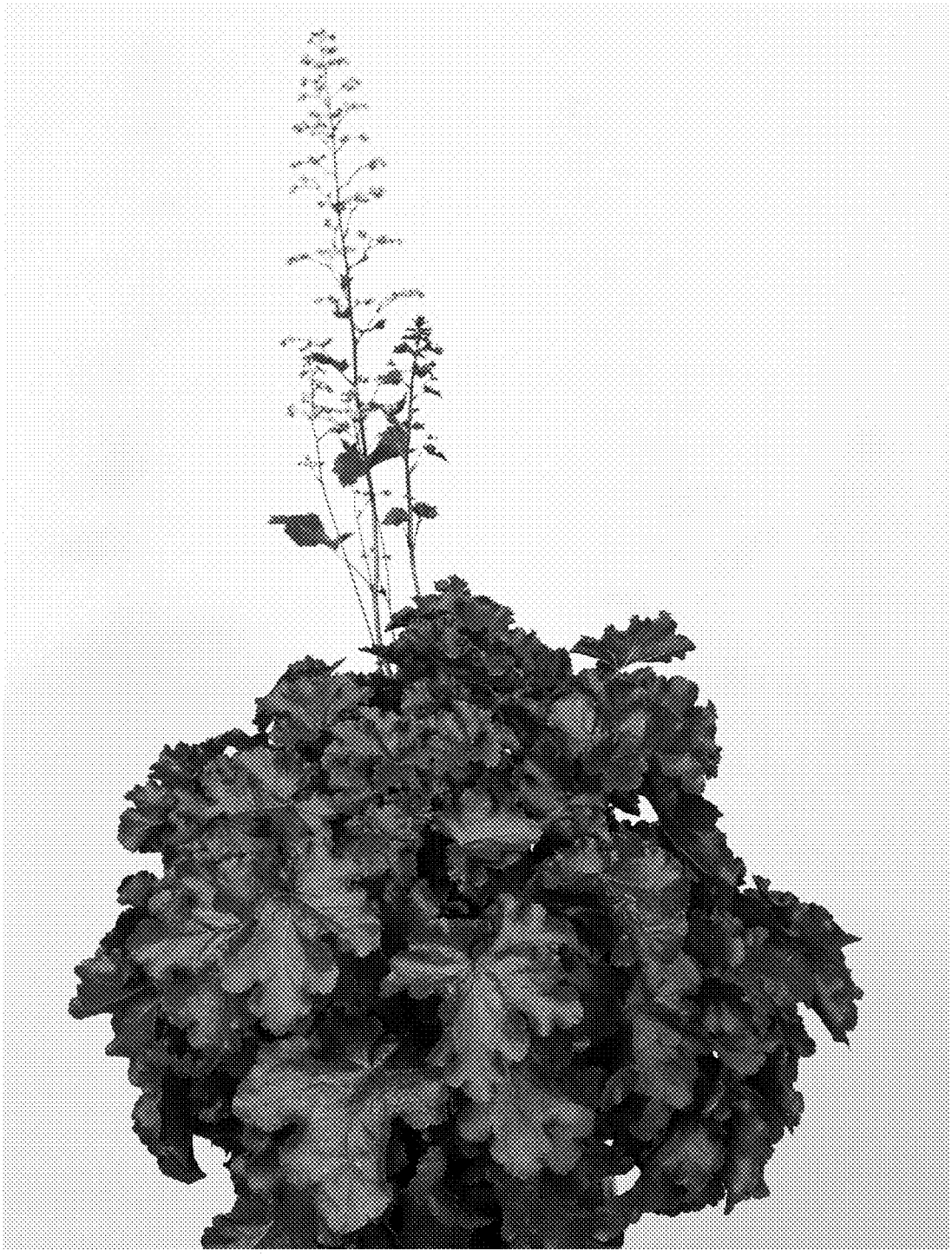

The photograph in FIG. 1 provides a side view of the plant of 'Toncka 308' in bloom.

Figure 2:
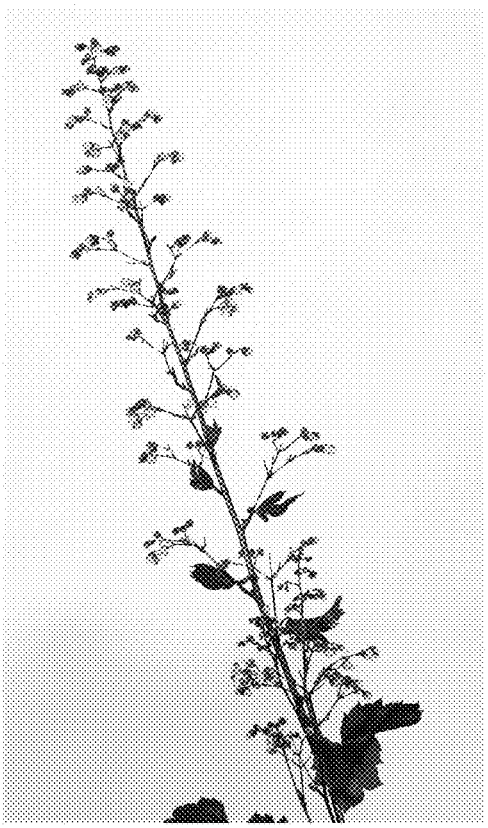

The photograph in FIG. 2 provides a close up of an inflorescence of 'Toncka 308'.

Figure 3:
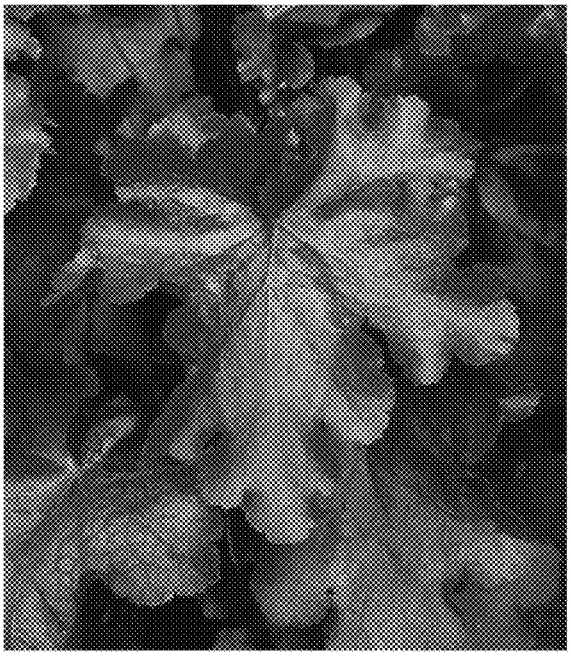

The photograph in FIG. 3 provides a close up view of a leaf of 'Toncka 308'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—8 weeks in midsummer in The Netherlands.

*Plant type*.—Herbaceous perennial.

*Plant habit*.—Globular with inflorescences held above the foliage.

*Height and spread*.—An average of 35 cm in height (soil level to top of foliar plane), average of 65 cm in height (soil level to top of floral plane) and 70 cm in spread as an 18 month-old plant.

*Cold hardiness*.—At least in U.S.D.A. Zone 3.

*Diseases and pests*.—No susceptibility or resistance to pests or diseases has been observed.

*Root description*.—Fibrous roots on woody rootstalks, 158D in color.

*Propagation*.—Tissue culture.

*Root development*.—An average of 3 weeks for root initiation and 6 weeks to produce a rooted cutting.

*Growth rate*.—Vigorous.

*Branching habit*.—Flowering stems emerge from basal rosette, an average of 5 rosettes per plant, no lateral branches.

Foliage description:

*Leaf shape*.—Orbicular, very slightly concave.

*Leaf division*.—Simple.

*Leaf base*.—Hastate, lobes moderately to strongly touching.

*Leaf apex*.—Mucronate.

*Leaf venation*.—Laciniate, upper surface 177A, lower surface 197A.

*Leaf margins*.—Crenate with mucronate tips on each tooth, moderately to strongly coarsely undulate.

*Leaf attachment*.—Petiolate.

*Leaf arrangement*.—Alternate in basal rosettes.

*Leaf lobes*.—Lobed, 7, occasionally 9 lobes, medium in depth, divergent, lobe margins free to touching.

*Leaf surface*.—Both surfaces smooth, moderately velvety, non-rugose, moderately glossy, pubescent, sparsely covered with very short strigose hairs 0.3 mm in length, too small to measure color.

*Leaf color*.—Young upper surface; 178A, young lower surface; 187C, mature upper surface; a blend of N186C and 200B, fading in summer into fall; 200C, slightly tinged 146A, mature lower surface; 187B, fading to a blend of N186D and 187B later in summer into fall.

*Leaf size*.—An average of 14.1 cm in length and 13.9 cm in width.

*Leaf quantity*.—An average of 8 per basal rosette.

*Petioles*.—An average of 19.5 cm in length and 3 mm in diameter, medium strength, both surfaces moderately glossy, upper surface color 187B, lower surface color 182B, tinged towards the distal end 197A, moderately covered with short, soft strigose hairs an average of 0.5 mm in length, too small to measure color.

*Stipules*.—Leafy stipule at the base of each leaf, average 2.1 cm in length, average 5 mm in width, acute tip, color; 71A, margins 70C to 70D.

Flower description:

*Inflorescence type*.—Numerous small bell-shaped flowers arranged on panicles on peduncles emerging from a basal rosette.

*Inflorescence size*.—An average of 64.7 cm in height and 14.6 cm in diameter.

*Inflorescence number*.—An average of 16.

*Flower fragrance*.—None.

*Flower quantity*.—Average of 400 flowers per flowering stem.

*Flower Lastingness*.—Average of one week.

*Flower buds*.—Obovate in shape, an average of 4 mm in length and 3 mm in diameter, color; 182D, lower ⅔rd 185B, surface is matte and densely covered with very short glandular hairs; an average of 0.2 mm in length and too small to measure color.

*Flower aspect*.—Outward to nodding.

*Flower type*.—Single, campanulate.

*Flower size*.—Average of 9 mm in height and diameter, 6 mm in length.

*Petals*.—Average of 5, rotate arrangement and implanted in the hypanthium at base, oblanceolate in shape, margin is entire, apex is acute, base is long acuminate, upper and lower surface is glabrous, smooth and matte, an average of 4 mm in length and 1 mm in width, color when opening and fully open upper and lower surface; NN155D.

*Calyx*.—Campanulate, sepals fused to hypanthium, 6 mm in length, 4 mm in diameter.

*Sepals*.—An average of 5, lower 30% fused into campanulate hypanthium, ovate in shape, an average of 5 mm in length and 3 mm in width, margin is entire and fused into hypanthium, apex is obtuse, color; when opening and fully open upper surface 186D, lower half 186A, tip 145B, when opening and fully open lower surface 186C, top and lower half 186A, outer tip 146D, both surfaces are matte and densely covered with very short glandular hairs an average of 0.2 mm in length and to small to measure color.

*Peduncle*.—An average of 80.5 cm in length and 3 mm in diameter, color; 200B, primary flower aspect 60°, secondary peduncle aspect to main peduncle 32.5°, moderate in strength, surface moderately glossy and moderately covered with very short soft glandular hairs; average of 0.75 mm in length and NN155D in color.

*Pedicels*.—An average of 3 mm in length and 0.5 mm in diameter, 177D in color, primary flower aspect straight on top of secondary pedicel, secondary and tertiary flower aspect is 45°, moderate in strength, surface matte and densely covered with very short soft glandular hairs; an average of 0.2 mm in length and too small to measure color.

Reproductive organs:

*Gynoecium*.—Pistils; 2, 5 mm in length, stigma; club-shaped, 0.2 mm in diameter, style; an average of 4.75 mm in length and NN155D in color, ovary; 147C to 147D in color.

*Androecium*.—Stamens; 5, anthers; ovate in shape, average of 0.3 mm in length and width, NN155D in color, filament; 2 mm in length and NN155D in color, pollen; low in quantity, 28A in color.

*Seed/fruit*.—No fruit or seeds have been observed to date.

It is claimed:

1. A new and distinct cultivar of *Heuchera* plant named 'Toncka 308' as herein illustrated and described.

* * * * *